(12) United States Patent
Joung

(10) Patent No.: US 7,498,582 B2
(45) Date of Patent: Mar. 3, 2009

(54) ADJUSTABLE FOCAL LENGTH PINHOLE COLLIMATOR

(75) Inventor: Jinhun Joung, Algunquin, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/386,407

(22) Filed: Mar. 22, 2006

(65) Prior Publication Data

US 2007/0221853 A1 Sep. 27, 2007

(51) Int. Cl.
*G21K 1/02* (2006.01)
*G01T 1/202* (2006.01)
(52) U.S. Cl. .................................. 250/363.1; 378/149
(58) Field of Classification Search ............ 250/363.01, 250/363.02, 363.04, 363.09, 363.1, 336.1, 250/361 R, 505.1; 378/147, 149
See application file for complete search history.

(56) References Cited

U.S. PATENT DOCUMENTS

| 4,321,473 A | * | 3/1982 | Albert | 378/149 |
| 4,823,017 A | * | 4/1989 | Hsieh | 250/363.03 |
| 7,166,846 B2 | * | 1/2007 | Engdahl et al. | 250/363.1 |
| 2006/0000978 A1 | * | 1/2006 | Engdahl et al. | 250/363.1 |
| 2006/0023832 A1 | * | 2/2006 | Edic et al. | 378/7 |

* cited by examiner

*Primary Examiner*—David P Porta
*Assistant Examiner*—Mark R Gaworecki
(74) *Attorney, Agent, or Firm*—Peter L. Kendall

(57) ABSTRACT

A pinhole collimator is provided that eliminates or at least minimizes the need for collimator exchange, to manage system sensitivity versus spatial resolution tradeoff, and to control imaging FOV (field of view) depending on object size by controlling the focal length of the collimator. There is also provided a detector system is that includes a detector, a collimator, and means for changing the focal length. Various means for changing the focal length are also identified. The collimator can have a plurality of apertures in a top plate, each aperture with its own collimator septa. Additionally, there is provided a medical imaging system that includes the detector system and collimator of the present invention. The nuclear medical imaging systems can have a hand-held detector assembly and be portable.

29 Claims, 12 Drawing Sheets

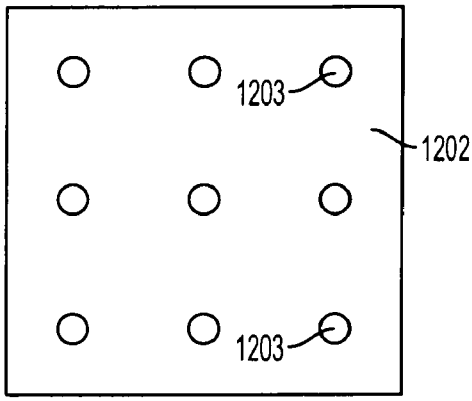
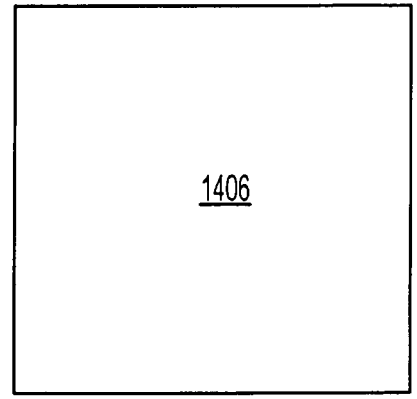
FIG. 12
FIG. 14
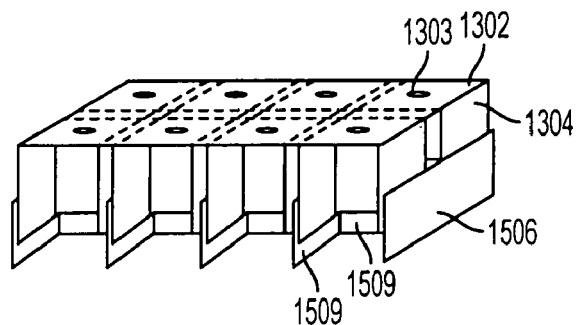
FIG. 16
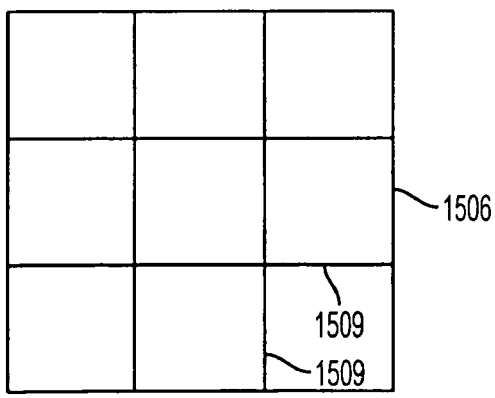
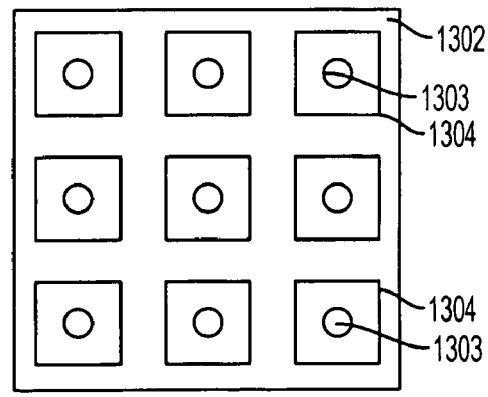
FIG. 15
FIG. 13

ADJUSTABLE FOCAL LENGTH PINHOLE COLLIMATOR

FIELD OF THE INVENTION

The present invention relates generally to gamma ray detectors, and more specifically to gamma ray collimation in combination with a detector, for example, semiconductor detectors, in nuclear medicine.

BACKGROUND OF THE INVENTION

Semiconductor detectors are attractive and have become popular for the field of nuclear medicine because of their very small size and weight, excellent spatial resolution, and direct conversion of gamma photons into electrical signals. Those features make such a detector an ideal applicant for small animal imaging or tiled detectors where FFOV (full field of view) is achieved by tiling many small and modular detectors together because the required imaging FOV is larger than the size of typical semiconductor detectors.

However, conventional collimation methods are not adequate to fully utilize the advantages of small and independent modular detectors. In addition, conventional collimation methods require collimator exchanging and increase system cost due to the need for multiple sets of collimators depending on isotope energy and imaging options. Further, the collimator exchanging requirement significantly limits system design. For instance, in full or partial ring-type systems, it is a great challenge to exchange collimators.

Therefore, there exists a need to more filly utilize the use of semiconductor detectors and minimize collimator exchanging.

SUMMARY OF THE INVENTION

In one aspect of the present invention, a novel pinhole collimator is disclosed that eliminates or at least minimizes the need for collimator exchange, to manage system sensitivity versus spatial resolution tradeoff, and to control imaging FOV (field of view) depending on object size by controlling the focal length of the collimator.

In another aspect of the invention, a detector system is disclosed that includes a detector, a collimator, and means for changing the focal length.

In yet another aspect of the invention, a medical imaging system is disclosed that includes the detector system.

Accordingly, there is provided a collimator for use with a detector of nuclear radiation, where the detector has a top surface, including a collimator surface having at least one aperture located in a plane parallel to the top surface, wherein when the collimator is used with the detector, the plane and the top surface are spaced apart by a focal distance f. The collimator also has at least one collimator septum defining the side wall or walls of the collimator and means for changing the focal distance f to adjust the focal length of the collimator. Various means can be used.

In one embodiment the at least one collimator septum is a first septal tube and the means for changing the distance f includes the first septal tube, a top plate with a centrally located threaded hole, and an aperture tube having male threads, a first opening and a second opening. The aperture tube threadedly engages the threaded hole. The top plate is secured to one end of the first septum opposite the top surface of the detector. In this embodiment, the at least one aperture is the first opening, which is opposite the top surface and changing the relative position of the first opening to the top surface changes the focal distance f. This relative position is changed by screwing or unscrewing the aperture tube.

In another embodiment, the collimator has a first septal tube and a second septal tube that is smaller in cross-section than the first septal tube such that the second septal tube is received within the first septal tube. Alternatively, the collimator has a top plate with a plurality of apertures and a corresponding number of first septa attached to the top plate around a respective one of the plurality of apertures and there is a corresponding second septum for each first septum.

In these embodiments, the means for changing the distance f is means for changing the relative position of the second septum within the first septum. This can be done various ways, for example, using a cam and cam follower assembly, using male threads on the second septum and female threads on the first septum, and using a positioner having an actuator and a rod. When a positioner is used, the actuator is attached to one of the two septa and the rod is attached to the other septa, for example, using a tab. The positioner can come in various forms, for example, an electric motor and a threaded rod, a hydraulic or air operated actuator and a rod that is extended or contracted by the action of the actuator. When an electric motor is used as the actuator, the rod is rotated by the motor and the rod has a threaded portion that threadedly engages a threaded hole in the tab.

The cross-section of the first and second septa is selected from the group of circle, square, rectangle and other polygons.

The collimator can also have a top plate with the at least one aperture and is located opposite the top surface of the detector. In one embodiment, the top plate has one aperture. In this case, the top plate can be removable and replaceable with a second top plate having a different sized aperture.

Also provided is a detection system for nuclear radiation that comprises a nuclear radiation detector, a collimator, and means for changing the focal distance f to adjust the focal length of the collimator. The detector has at least one edge and a top surface. The collimator has a collimator surface having an aperture located in a plane parallel to the top surface, wherein the plane and the top surface are spaced apart by a focal distance f. The collimator also has at least one collimator septum defining the side wall or walls of the collimator. If the collimator has a circular cross-section, then it has one septum that defines the wall of the collimator. The system also has means for changing the focal distance f to adjust the focal length of the collimator.

In one embodiment, the collimator comprises the means for changing the distance f. The various embodiments discussed above for the collimator can be used in this embodiment of the detection system.

In another embodiment, the means for changing the distance f is means for moving the detector normal to the plane. As with the collimator embodiments, the detector can be moved using a positioner, a cam and cam follower assembly, and various threaded assemblies using threaded rods and tabs each with a threaded hole.

The nuclear radiation detector can be a single or tiled detector. Additionally, the detector can be a semiconductor detector or a scintillation crystal.

Further, there is provided a nuclear imaging system comprising at least one detection system described above. In one embodiment the nuclear imaging system comprises a handheld device including a detection system according to the present invention. In another embodiment, the nuclear imaging system is portable. In yet another embodiment, the nuclear imaging system according to the present invention is for the nuclear imaging of a woman's breast and includes at least one detection system of the present invention which is of a size appropriate for the scanning of the breast. This embodiment can optionally means for selectively tilting the at least one detection system such that the top surface is selectively tilted or parallel to the axis of the breast. In another embodiment, the nuclear imaging system has at least two detection systems according to the present invention.

BRIEF DESCRIPTION OF THE FIGURES

FIG. 12 is a pictorial representation of another embodiment of the present invention showing a top elevation of a top plate with multiple pinhole apertures with no septa attached thereto.

FIG. 13 is a pictorial representation of another embodiment of the present invention showing a bottom elevation of a top plate with multiple pinhole apertures with each aperture having a first septa attached to the top plate.

FIG. 14 is a pictorial representation of another embodiment of the present invention showing a top elevation of a second septa for a tiled detector.

FIG. 15 is a pictorial representation of another embodiment of the present invention showing a top elevation of a grid of second septa for a tiled detector.

FIG. 16 is a pictorial representation of another embodiment of the present invention showing a partial cross-section of the combination of a top plate having a plurality of first septa shown in FIG. 13 in telescoping relationship with a second septa shown in FIG. 15 for a tiled detector.

DETAILED DESCRIPTION OF THE PREFERRED EMBODIMENTS

Figure 1A:
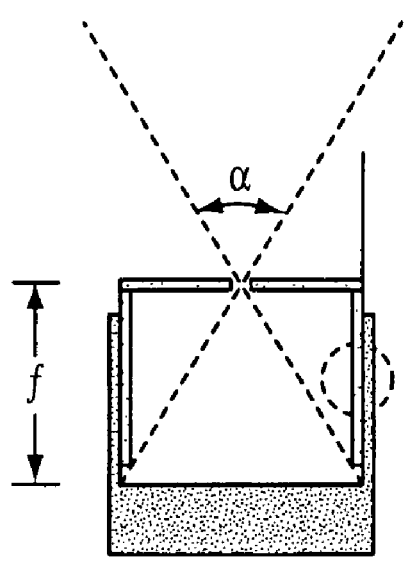
FIG. 1a is a pictorial representation of one embodiment of the present invention showing a pair of tubular septa in telescoping relationship in a contracted position with an acceptance angle $\alpha_1$.
Figure 1B:
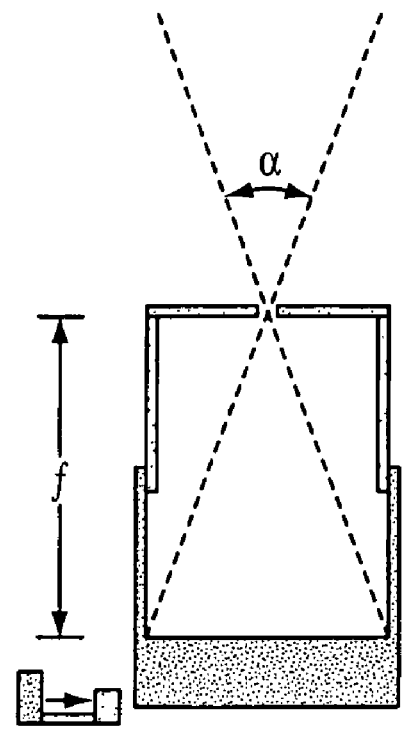
FIG. 1b is the pictorial representation shown in FIG. 1a with the pair of tubular septa in telescoping relationship in an extended position with an acceptance angle $\alpha_2$.

FIGS. 1a and 1b show a graphical representation of an embodiment of the invention, that is an adjustable pinhole collimator/detector assembly 100. The assembly 100 includes a pinhole plate 102 having a pinhole 103 and outer walls 104 and 106 between the pinhole plate 102 and the surface 107 of the detector 108. Both the plate 102 and walls 104 and 106 are made of materials that block radiation, for example, lead and tungsten. The outer walls have a first (or inside) septa 104 and a second (or outside) septa 106. The first and second septa 104, 106 can be extended as shown in FIG. 1(b). There is a mechanical and/or electrical mechanism (not shown) between septa 104, 106 to ensure precise extension of septa 104, 106. The focal length "f" in this embodiment is controlled by extending/contracting first septa 104. Any kind of mechanism can be employed to extend/contract the first septa 104 relative to the second septa 106.

Figure 1C:
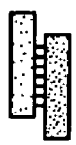

Since the detector area is relatively small (about 25 to about 100 cm²) compared to typical pinhole diameter, i.e., 2-3 mm, acceptance angle is determined by the height of the septa, denoted as "f", in FIGS. 1*a* and 1*b*. Once the first and second septa 104, 106 are extended (FIG. 1(*b*)), acceptance angle "α" is decreased so that both sensitivity and FOV are decreased while spatial resolution improves due to the magnification factor. In contrast, as the focal length "f" is decreased (FIG. 1(*a*)), sensitivity and FOV are improved at the expense of sacrificing spatial resolution.

The detector 108 can be a semiconductor detector or a scintillation crystal, both of which are well-known to those skilled in the art. U.S. Pat. Nos. 5,245,191 and 5,825,033 disclose examples of semiconductor detectors.

Figure 2:
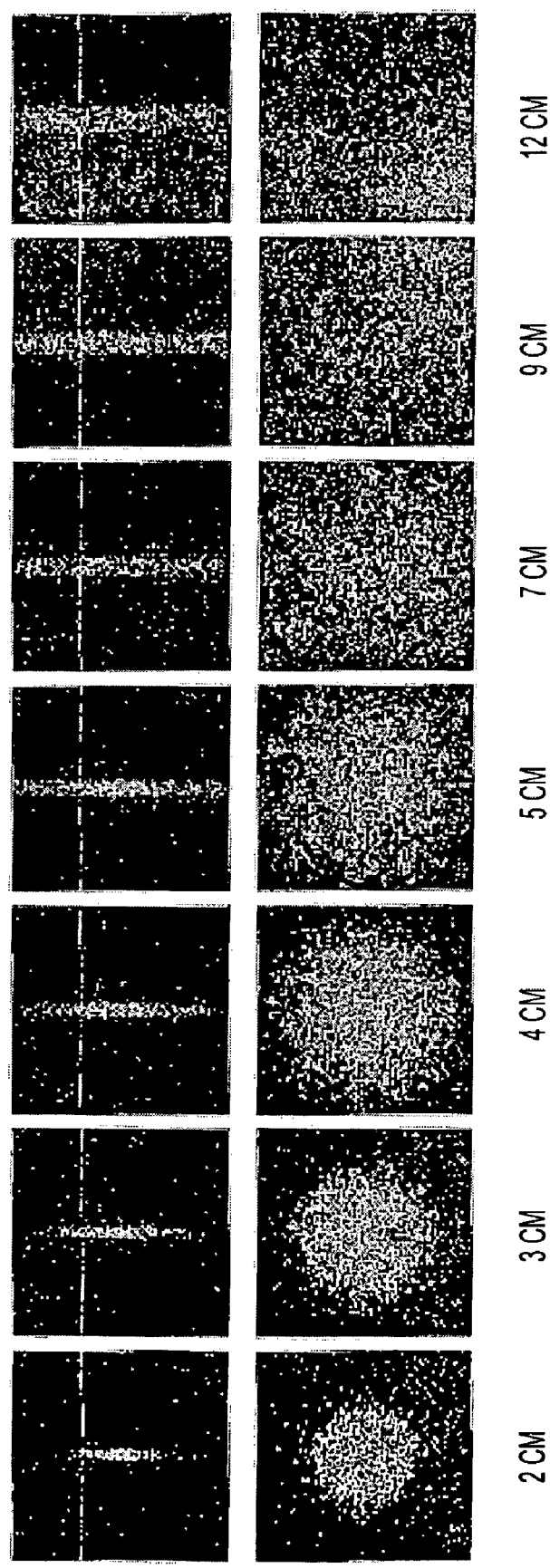
FIG. 2a shows the Monte Carlo simulation results using a line source and an adjustable collimator and a sphere source and adjustable collimator as shown in FIGS. 1a and 1b with the pair of tubular septa in telescoping relationship adjusted to different focal lengths "f".

Monte Carlo Simulation:

Monte Carlo simulations were conducted to demonstrate the sensitivity and spatial resolution trade-off as a function of the pinhole collimator focal length "f". FIG. 2 top and bottom rows show Monte Carlo simulation results of line and sphere radiation sources for spatial resolution and sensitivity measurement, respectively.

The dimension of the sphere source was 2.5 cm in diameter with uniform activity concentration and the line source was a cylinder 5 cm long with 0.2 mm in diameter. A total of 1.85 mCi of m99Tc was injected and 140 KeV gamma photons with 10% energy blurring were collected for 10 seconds in both cases. Detector surface was 5×5 cm$^2$ with 0.39 mm pixel size. Pinhole size was a cylinder 2 mm in diameter and 3 mm long (depth or height). As a scintillator, CsI(T1) was simulated with 7 mm thickness.

The FWHM (full width at half maximum) of the line source became wider as the focal length increased. However, due to the magnification factor increasing as focal length increased, the adjusted FWHM after considering magnification factor improved as focal length increased.

Figure 3A:
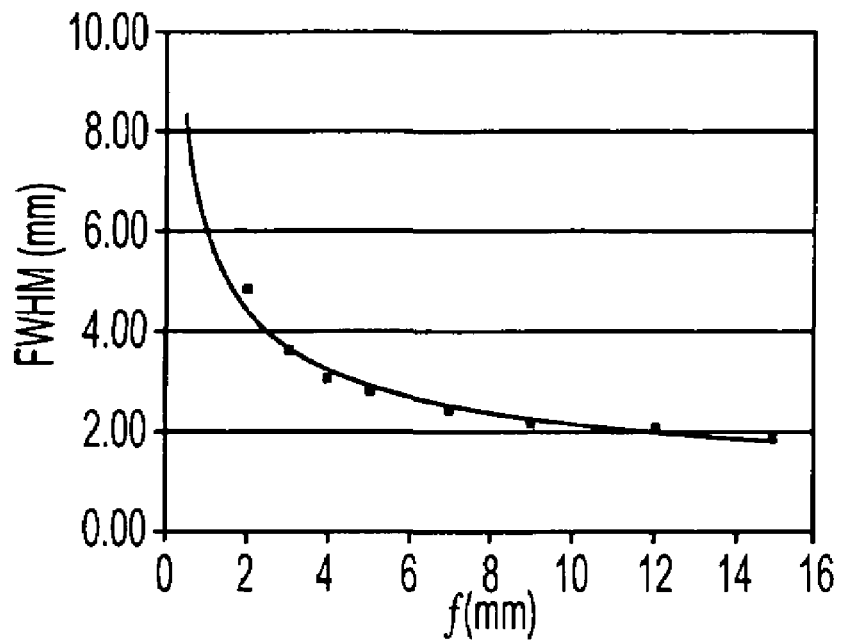
FIG. 3a is a graphical presentation of the spatial resolution as a function of focal length "f".

The sensitivity and resolution trade-off graph as a function of collimator focal length is shown in FIGS. 3*a* (spatial resolution) and 3*b* (sensitivity). Spatial resolution improved as the focal length "f" increased at the cost of sensitivity degradation as anticipated. For this size detector, the optimum imaging range was determined to be 5 cm to 12 cm, since there were no dead corners.

Figure 4A:
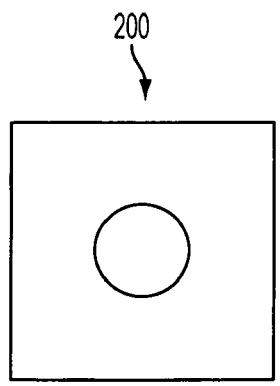
FIGS. 4a, 4b and 4c show a top elevation of pinhole collimator embodiments according to the present invention having a square, a circular, and a hexagonal cross-section, respectively.
Figure 4B:
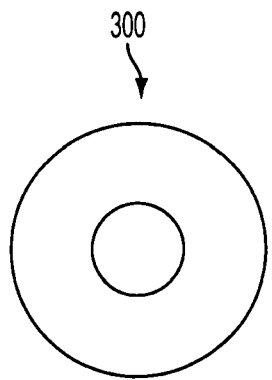
Figure 4C:
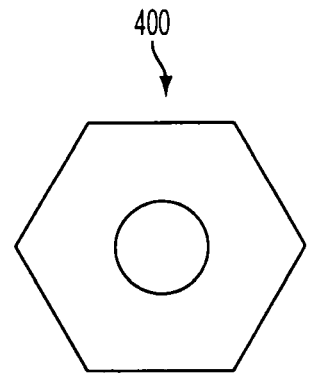

The pinhole collimators of the present invention can have a variety of cross sectional shapes. Referring now to FIGS. 4*a*, 4*b* and 4*c*, there are shown a top elevation of pinhole collimator embodiments according to the present invention having a square 200, a circular 300, and a hexagonal 400 cross-section, respectively.

Figure 5A:
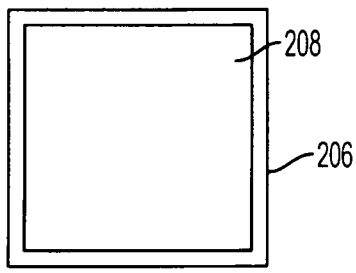
FIG. 5a is a pictorial representation of a single detector.
Figure 5B:
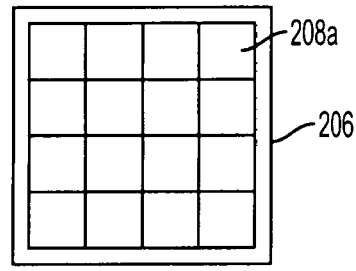
FIG. 5b is a pictorial representation of a tiled detector.

The pinhole collimators of the present invention can be used with a single detector or a tiled detector. FIG. 5*a* shows a pictorial representation of a single detector 208 with a second septa 206 having a square-shaped cross section. In an alternative embodiment, a tiled detector 208*a* is shown in FIG. 5*b* with a second septa 206 having a square-shaped cross section.

Figure 3B:
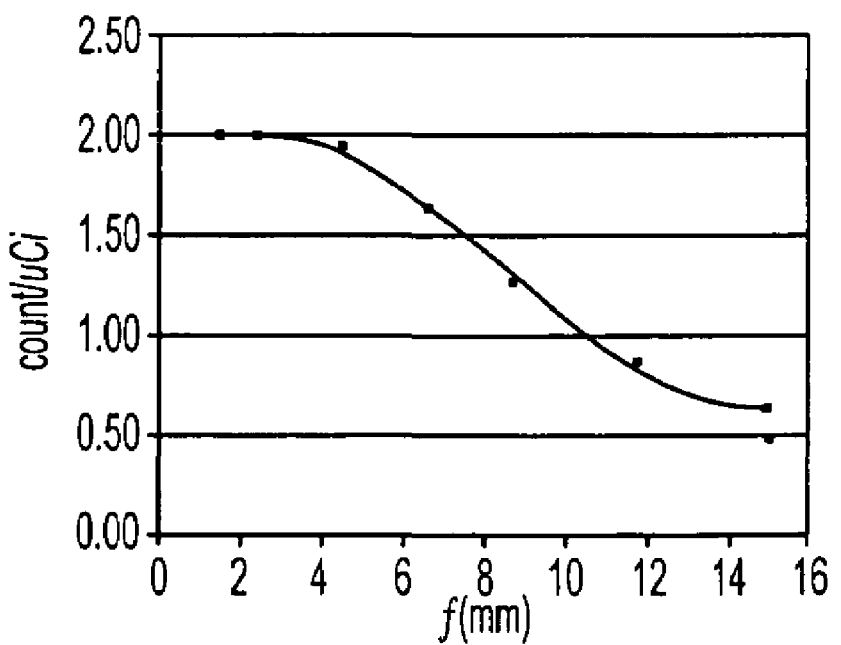
FIG. 3b is a graphical presentation of the sensitivity trade-off as a function of focal length "f".
Figure 6:
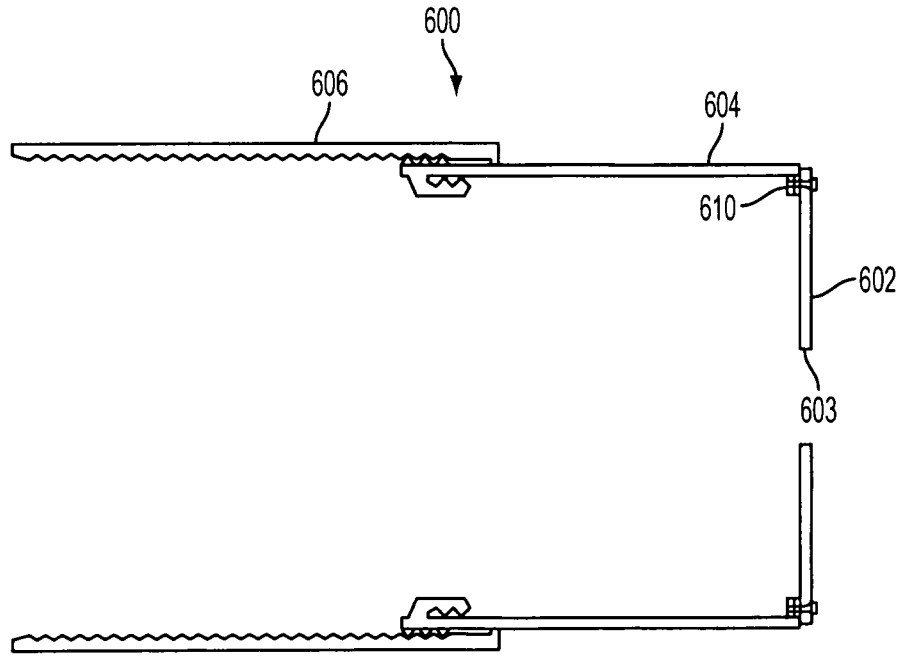
FIG. 6 is a pictorial representation of another embodiment of the present invention showing the embodiment of FIG. 1 with removable top plate to change the size of the pinhole aperture and where the first and second septa are threadedly engaged to adjust the focal length of the collimator.

A variety of methods and mechanisms are available for adjusting the focal length or distance between the aperture of the collimator and the detector surface. Several of these involve telescopically extending or contracting the first septa relative to the second septa. For example, FIG. 6 shows a pictorial representation of a collimator 600 having a circular cross-section where the first septa 604 and second septa 606 are threadedly engaged to adjust the focal length of the collimator 600. This is similar to that disclosed in U.S. Pat. No. 6,707,993 and shown in FIG. 3 thereof, which is hereby incorporated by reference. Additionally, top plate 602 is held by screws 610 to the first septa 604 and removable to change the size of the pinhole aperture 603.

Figure 7:
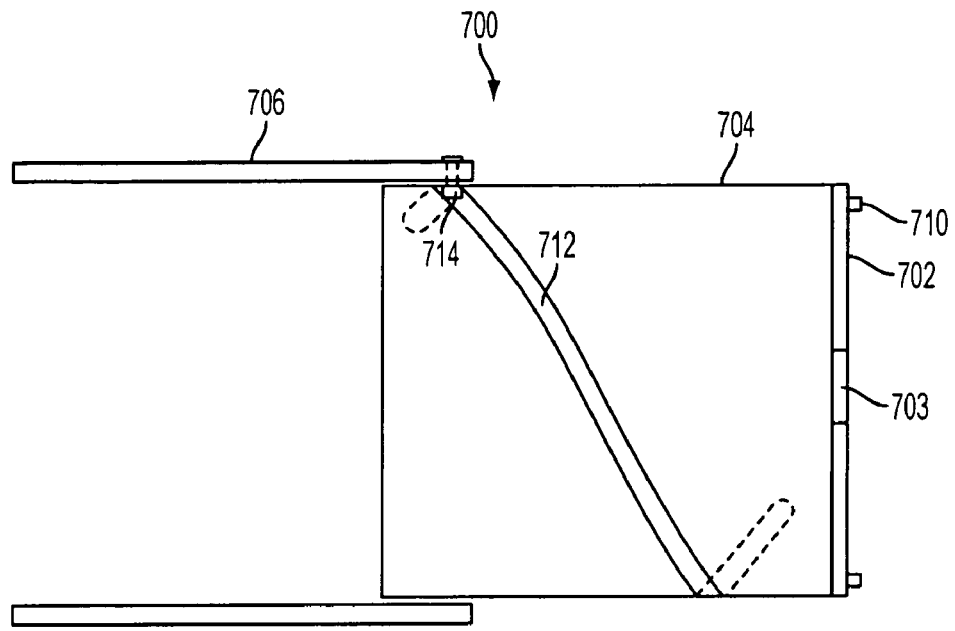
FIG. 7 is a pictorial representation of another embodiment of the present invention similar to that shown in FIG. 6 with the exception that a cam follower and a spiral cam are utilized to adjust the focal length of the collimator.

Referring now to FIG. 7, there is shown a pictorial representation is partial cross-section of a collimator 700 having a circular cross-section where the first septa 704 has a spiral cam 712 with a cam follower 714 secured to the second septa 706. As the first septa 704 is rotated, the cam follower 714 follows the path defined by the spiral cam 712 causing the first septa 704 to extend or contract relative to the second septa 706 to adjust the focal length of the collimator 700. Thus, the first and second septa 704, 706 operate like the barrels of a telephoto camera lens, see for example, U.S. Pat. No. 6,243,214 and FIG. 1 thereof, which is hereby incorporated by reference. More than one spiral cams and associated cam followers can be used. Similar to collimator 600, top plate 702 is held by screws 710 to the first septa 704 and removable to change the size of the pinhole aperture 703.

Though spiral cams are limited to collimators hereof having circular shaped cross-sections, flat cams and associated cam follower as disclosed in U.S. Pat. No. 5,166,829 and shown in FIGS. 2 and 3 thereof, incorporated herein by reference, can be used with collimators of square, hexagonal and circular cross-sections.

Figure 8:
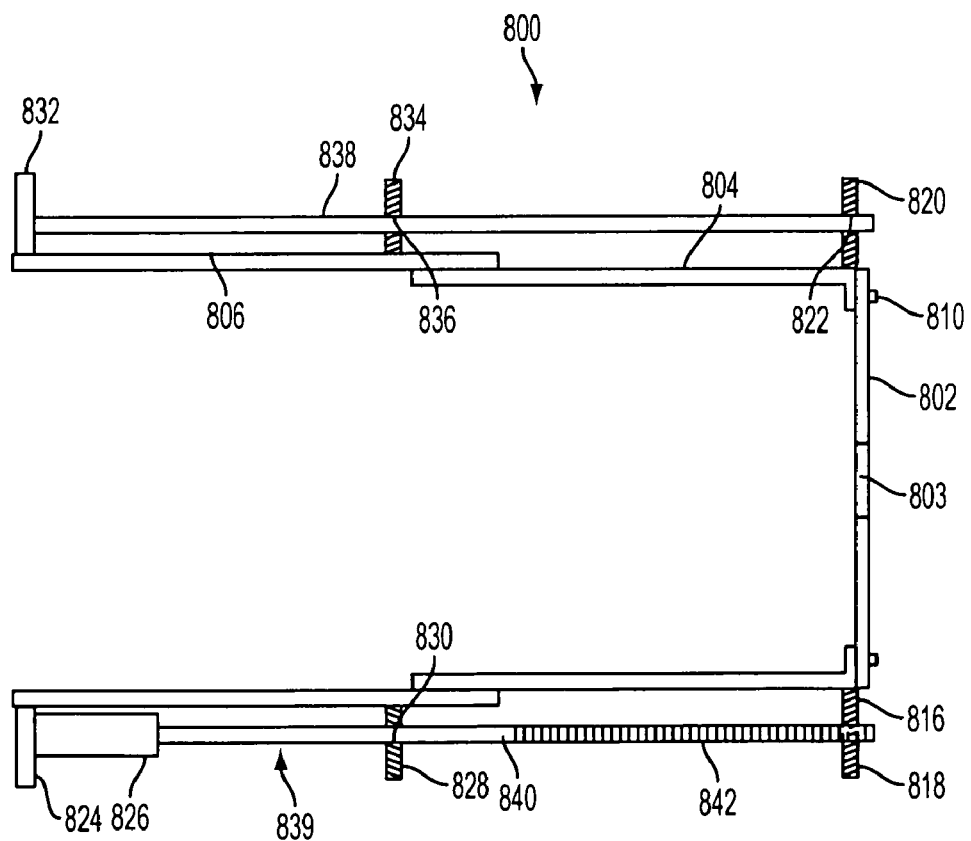
FIG. 8 is a pictorial representation of another embodiment of the present invention similar to that shown in FIG. 6 with the exception that a threaded tab on the first septa is threadedly engaged by a threaded shaft of an electric motor are utilized to adjust the focal length of the collimator.

Referring now to FIG. 8, there is shown a collimator 800 with a first septa 804 having a first tab 814 with a threaded hole 818 and a second tab 820 with a smooth hole 822. The collimator 800 also has a second septa 806 having a first base tab 824, a first upper tab 828 having a first smooth hole 830, a second base tab 832, and a second upper tab 834 with a second smooth hole 836. A guide rod 838 is secured at one end to the second base tab 832. The guide rod 838 extends through holes 836 and 822. An electric motor 826 is mounted on the first base tab 824 and has a shaft 839 with a smooth portion 840 and a threaded portion 842. The smooth portion 840 is received by the first smooth hole 830 and the threaded portion 842 threadedly engages the threaded hole 818. Thus, by operating the electric motor 826 to rotate the shaft threaded portion 842, the first septa 804 is extended or contracted relative to the second septa 806 to adjust the focal length of the collimator 800. The guide rod 838 cooperating with tabs 820 and 834 stabilizes the movement of the first septa 804 relative to the second septa 806. Alternatively or in addition for fine movement of the shaft 839, a thumbwheel can be attached to the end of the threaded portion 842. Further, the electric motor 826 can be omitted and the end of the smooth portion 840 opposite the juncture of the smooth portion 840 and the threaded portion 842 is rotatably secured to the first base tab 824 and the thumbwheel is used to rotate the shaft 839 to contract or extend the first septa 804 relative to the second septa 806. Top plate 802 with aperture 803 is removably secured to the first septa 804 with screws 810.

Figure 9:
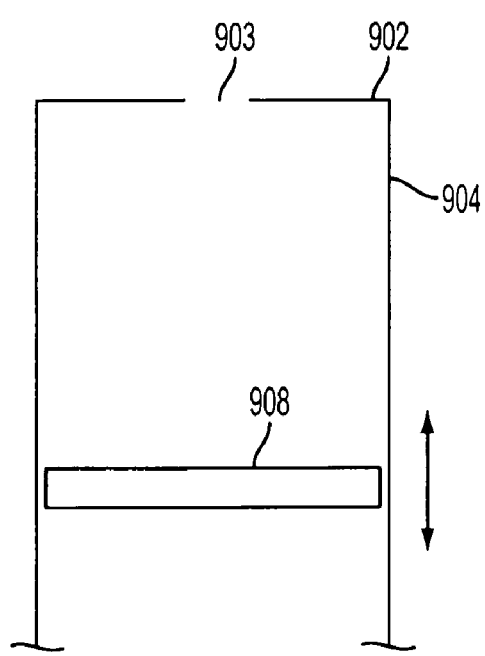
FIG. 9 is a pictorial representation of another embodiment of the present invention showing a tubular septa with an axially movable detector within the tubular septa where the focal length "f" is controlled by moving the detector within the tubular septa.

Referring now to FIG. 9, collimator 900 is shown having a septa 904 with a detector 908 that is axially movable within the septa 904 to adjust the focal length of the collimator 900. The collimator 900 has a top plate 902 with an aperture 903.

Figure 10A:
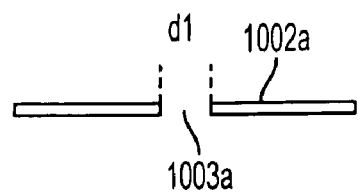
FIGS. 10a and 10b are pictorial representations of top plates having a pinhole of diameter $d_1$ and $d_2$, respectfully.
Figure 10B:
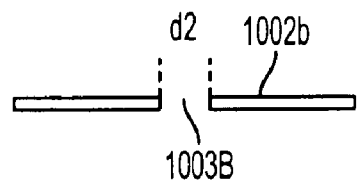

Referring now to FIGS. 10*a* and 10*b*, pictorial representations of top plates 1002*a* and 1002*b* having a pinhole 1003*a* and 1003*b* of diameter d$_1$ and d$_2$, respectfully, are shown. As noted above with regard to FIGS. 6, 7 and 8, the top plates of embodiments of collimators according to the present invention can be changed.

Figure 11A:
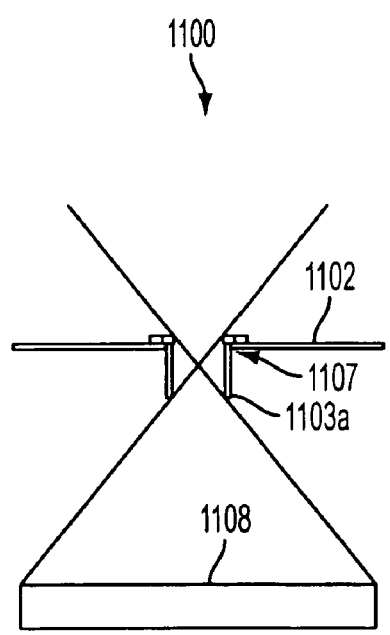
FIGS. 11a and 11b are pictorial representations of top plates having aperture inserts of different lengths to change the focal length of the collimator and the distance between the top plate and the detector are change accordingly to fully utilize the detector.
Figure 11B:
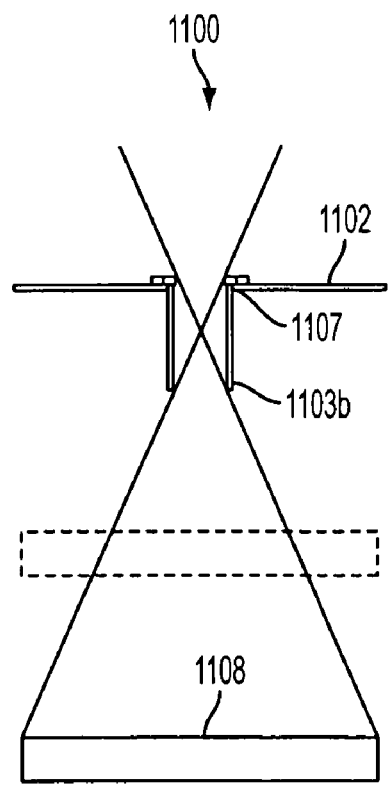

Referring now to FIGS. 11*a* and 11*b*, pictorial representations of top plate 1102 is shown with a threaded hole 1107 having aperture inserts 1103*a* and 1103*b* of different lengths to change the focal length of the collimator 1100 and the distance between the top plate 1102 and the detector 1108 are change accordingly to fully utilize the detector 1108 surface area. However, if the same distance were maintained between the top plate 1102 and the detector 1108, as in FIG. 11*a*, but using the aperture insert 1103b, the focal length of the collimator 1100 would be changed since the less of the amount of radiation entering the collimator 1100 is reduced due to the length of the aperture insert 1003b as shown in the ghost relief (dashed lines) of the detector 1108 corresponding to the position of the detector 1108 in FIG. 11a.

Referring now to FIG. 12, there is shown the top a top plate 1202 with multiple pinhole apertures 1203 with no septa attached thereto.

Figure 17:
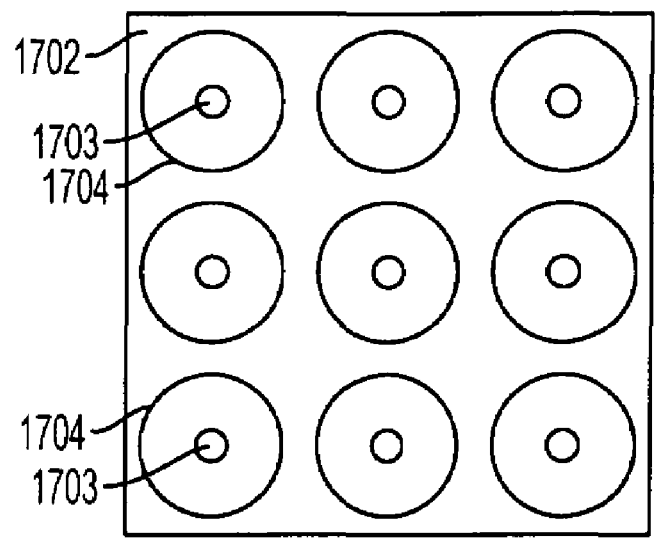
FIG. 17 is a pictorial representation of another embodiment of the present invention showing a bottom elevation of a top plate with multiple pinhole apertures with each aperture having a first septa attached to the top plate, which is similar to that shown in FIG. 13, except that in the present embodiment the first septa are each circular in cross-section rather than square as in FIG. 13.

Referring now to FIG. 13, there is shown the bottom a top plate 1302 with multiple pinhole apertures 1303 with each aperture 1303 having a first septa 1304 with a square cross-section shape attached to the top plate 1302. Referring now to FIG. 17, there is shown the bottom a top plate 1702 with multiple pinhole apertures 1703 with each aperture 1703 having a first septa 1704 with a circular cross-section shape, rather than square shaped as in FIG. 13, attached to the top plate 1702.

Referring now to FIG. 14, there is shown a second septa 1406 with no interior septa walls and septa 1406 is for use with a tiled detector array (for example, as shown in FIG. 5b).

Referring now to FIG. 15, there is shown the top a second septa 1506 having a plurality of interior septa walls 1509 arranged in a grid pattern for use with a tiled detector array (for example, as shown in FIG. 5b).

The first septa shown in FIGS. 12, 13 and 17 can be combined with a second septa as shown in FIGS. 14 and 15 for use with large surface area detectors or detector arrays. For example, referring now to FIG. 16, there is shown a partial cross-section of the combination of a top plate 1302 having a plurality of first septa 1304 shown in FIG. 13 in telescoping relationship with a second septa 1506 having interior walls 1509 shown in FIG. 15 for a tiled detector array (not shown). A combination of at least one electric motor having a threaded shaft and optionally at least one guide rod as shown in FIG. 8 can be used to adjust the relative position of the first septa (or top plate if no septa) and the second (or bottom) septa.

If the top plate 1202 of FIG. 12 were used with the second septa 1406 of FIG. 14 with a large surface area detector or a tiled detector array, aperture inserts like 1103a and 1103b can be used to control the acceptance angle of the radiation and the focal length of the collimator, either alone or in combination with adjusting the distance between the aperture and the detector surface.

Figures 18A, 18B:
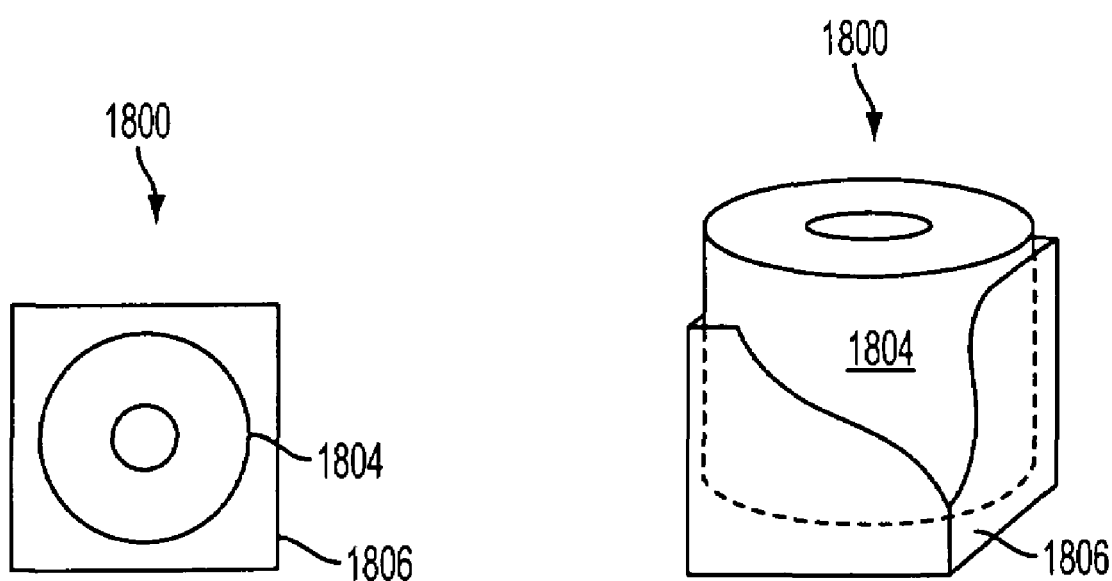
FIGS. 18a is a top elevation and 18b is a perspective elevation is partial cross-section of another embodiment of the present invention showing a pair of tubular septa in telescoping relationship where the first septa have a circular cross-section and the second septa has a square cross-section.

FIGS. 18a is a top elevation and 18b is a perspective elevation is partial cross-section of collimator 1800 having a first septa 1804 with a circular cross-section and the second septa 1806 with a square cross-section in a telescoping relationship. Means for adjusting the relative axial position of first septa 1804 and the second septa 1806 are not shown, but can be, for example, those means shown in FIGS. 7 and 8. However, one skilled in the art armed with the present disclosure can identify other means for adjusting this position.

Figure 19:
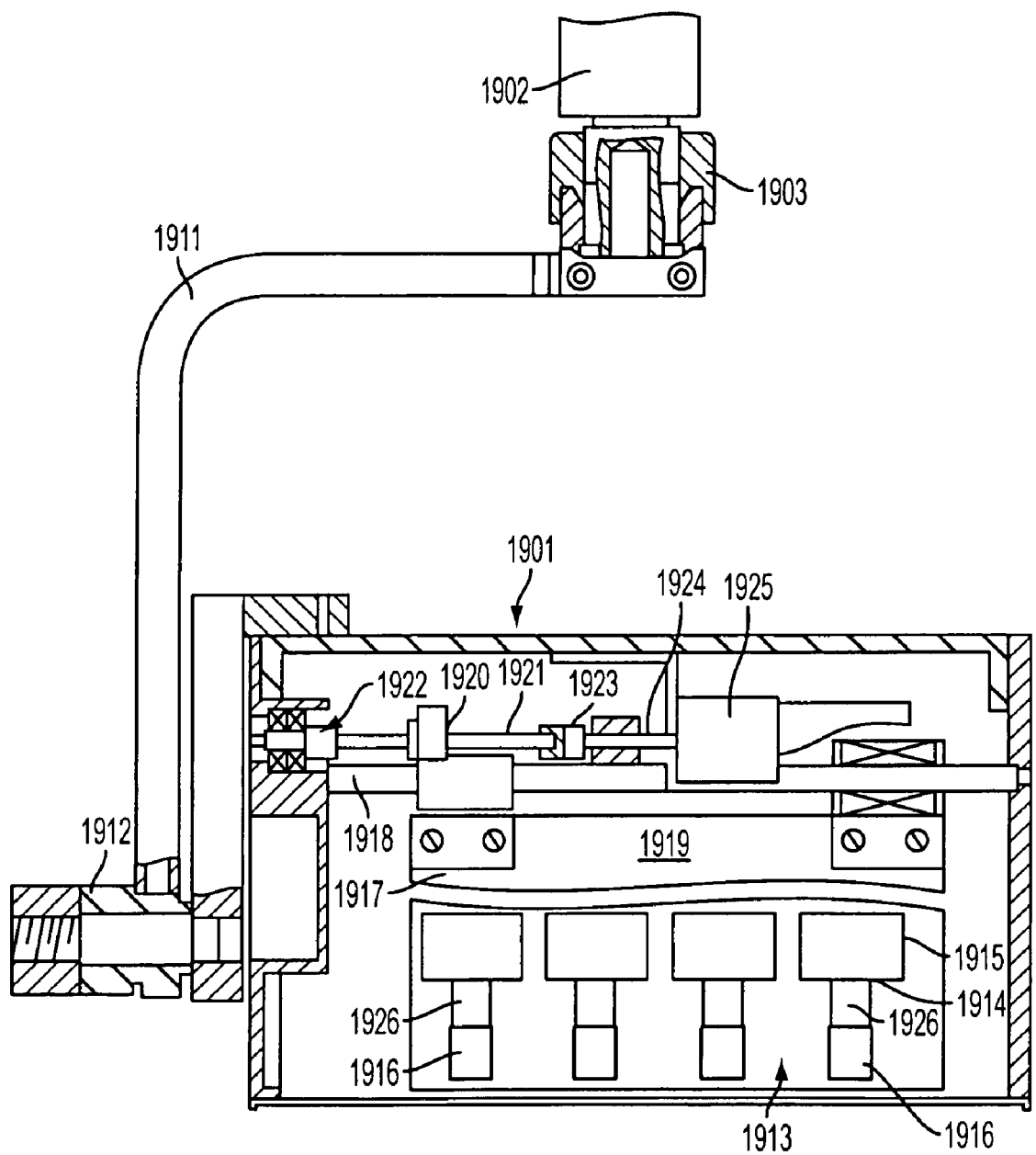
FIG. 19 is a section through the head of a light-weight mobile gamma-camera using an embodiment of an adjustable pinhole collimator according to the present invention.

The adjustable collimators of the present invention can be used with existing gamma-cameras used in nuclear medicine equipment. For example, the light-weight camera head and camera assemblies containing it disclosed in U.S. Pat. No. 5,939,724, hereby incorporated by reference, is modified herein to use an adjustable collimator of the present invention instead of a fixed collimator according to the prior art. Referring now to FIG. 19, there is shown a section through the head of a light-weight mobile gamma-camera head 1901, which is suspended from arm 1902 by means of a suspender member 1911 linked at one end to arm joint 1903 and at the other end to a joint 1912 of the camera head 1901. Joints 1903 and 1911 have a rotational degree of freedom of 360 degrees each.

The camera head 1901 has an array of four rows 1913 of detector units 1914, each unit having a detector plate with associated lead shielding marked together by numeral 1915, and associated collimator having a first septa 1916 and second septa 1926 which are telescopically adjustable to adjust the focal length of the collimator. The first septa 1916 and second septa 1926 have lead shielding and a quadrilateral bore of uniform cross-sectional shape with at least a portion of the second septa 1926 received within one end of the first septa 1916. The detector array is positioned on a carriage 1917 which is slidably mounted on a crossbar 1918 by means of cylindrical ball bearings 1919 one of which is outwardly screw-threaded and engaged by a toothed wheel 1920 keyed on a shaft 1921 held in at bearing 1922 and coupled at 1923 to the shaft 1924 of an electric servo motor 1925. The first septa 1916 can be adjusted relative to the second septa 1926 using a means as previously disclosed herein or other means with the skill of the art. The collimator of the present invention reduces the need to change collimators and allows the use of different focal lengths to better utilize the detector surface and with a single device to provide data to construct three dimensional images with appropriate commercially available software.

Figure 20:
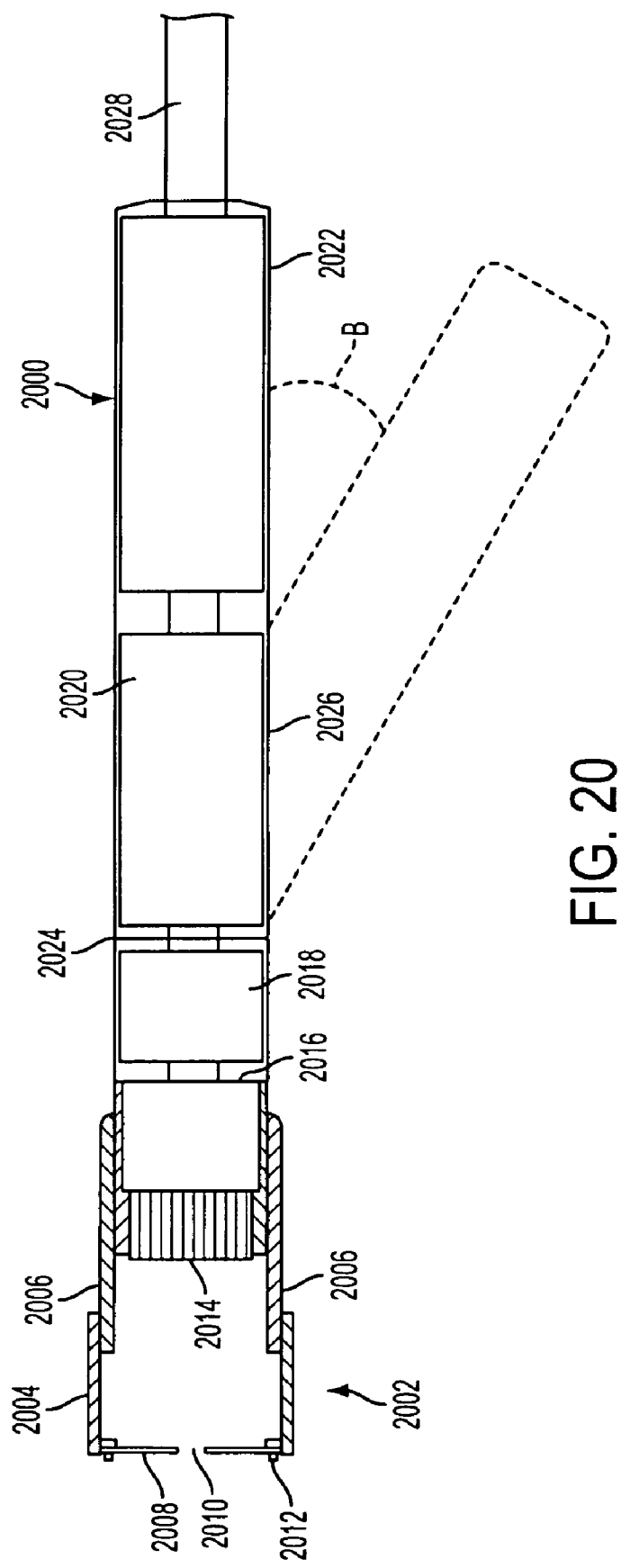
FIG. 20 is a cross sectional view of a portable imaging probe (a hand-held-imaging camera) including a collimator of FIG. 1a, a detector assembly (in this case a scintillator and a position sensitive photomultiplier-tube), and processing electronics housed in an inert packaging.

FIG. 20 depicts another example of portable imaging probe disclosed in U.S. Pat. No. 6,771,802, hereby incorporated by reference, adapted to use a collimator according to the present invention. There is shown a cross-sectional view of a portable imaging probe (a hand-held-imaging camera) 2000 that includes a collimator 2002 similar to that of FIG. 1a. The collimator 2002 has a first septa 2004 and a second septa 2006.

A top plate 2008 with an aperture 2010 is removable secured to the first septa 2004 with screws 2012. The probe 2000 has a scintillator 2014 coupled to a detector unit 2016, for example, a position sensitive photomultiplier tube, a DC-to-DC converter 2018, signal amplifier 2020 and signal shaper 2022 packaged in a housing 2024 made of an inert metal or plastic appropriate for intra-operative use. The handle 2026 can be straight or angled at angle B. The probe 2000 is connected via a cable 2028 to a computer (not shown). When a semiconductor detector is used as the detector unit 2016, the scintillator 2014 can be omitted and any associated processing electronics modified accordingly to operate with the semiconductor detector.

Figure 21:
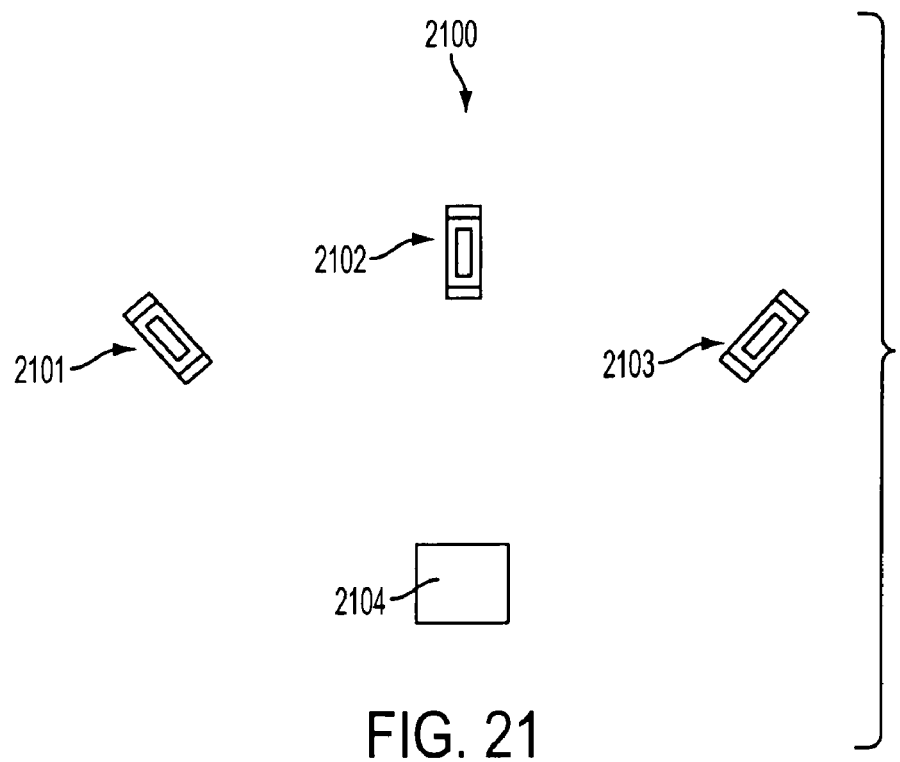
FIG. 21 is a simplified pictorial of another embodiment of the present invention having a plurality of detector/adjustable collimator assemblies in a nuclear medicine apparatus, for example, a SPECT (not showing gantry).

FIG. 21 depicts in simplified form a plurality of detector/adjustable collimator assemblies 2101, 2102 and 2103 in a nuclear medicine apparatus 2100, for example, a SPECT (not showing gantry). Additional detector/adjustable collimator assemblies can be present but are not shown. The target object or patient 2104 is positioned such that the plurality of detector/collimator assemblies 2101, 2102 and 2103 are approximately equidistant therefrom in an arcuate pattern.

Figure 22:
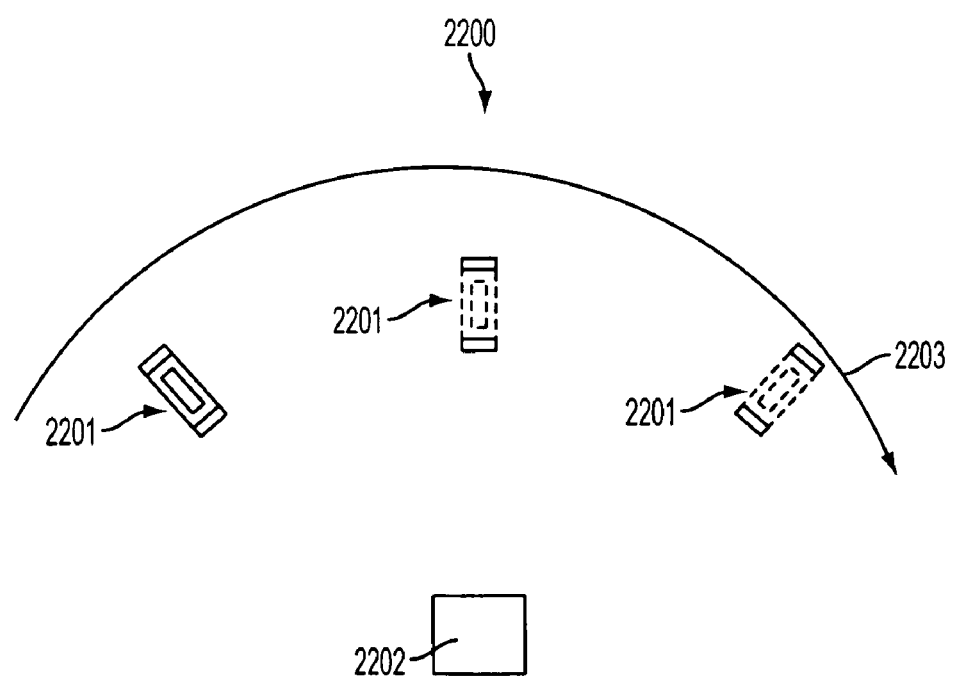
FIG. 22 is a simplified pictorial of another embodiment of the present invention having a single detector/adjustable collimator assembly in a nuclear medicine apparatus, for example, a SPECT (not showing gantry), where the detector/adjustable collimator is arcuately positionable about the target object or patient.

Alternatively, referring now to FIG. 22. there is depicted in simplified form a nuclear medicine apparatus 2200, for example, a SPECT (not showing gantry), having a single detector/adjustable collimator assembly 2201, where the detector/adjustable collimator assembly 2201 is arcuately positionable about the target object or patient 2202 along line 2203.

Figure 23:
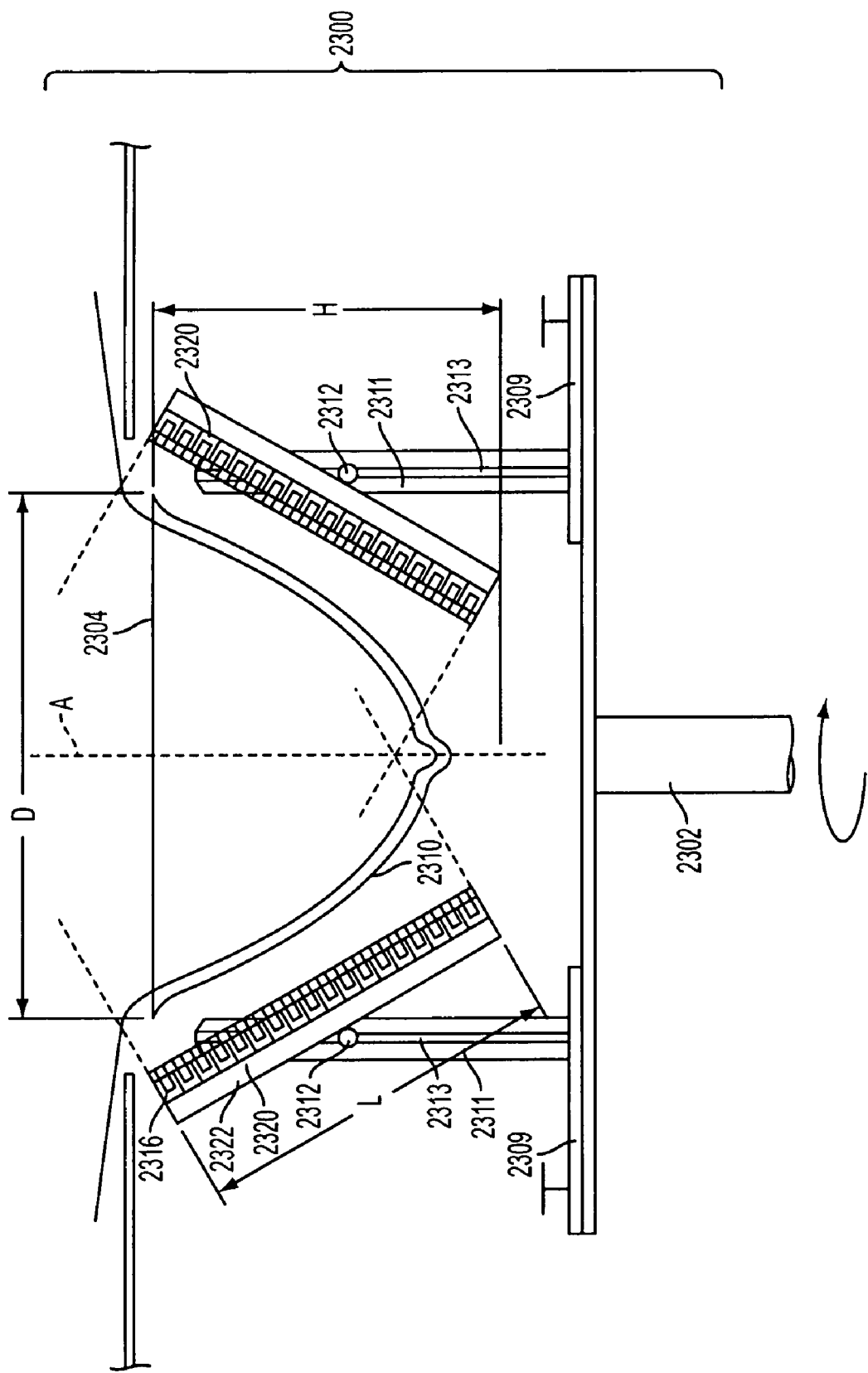
FIG. 23 is a schematic illustration of a tiltable camera-based SPECT system dedicated to the nuclear imaging of the breast and chest wall using an adjustable collimator similar to that shown in FIG. 16.

Reference is now made to FIG. 23 which is a schematic illustration of a camera-based SPECT system, dedicated to the nuclear imaging of the breast and chest wall, wherein the camera can be tilted. This camera is disclosed in U.S. Pat. No. 6,794,653, hereby incorporated by reference, and is modified herein to utilize an adjustable collimator according to the present invention. The camera-based SPECT system 2300 comprises two cameras 2320, 180 degrees apart. Each camera 2320 comprises an adjustable collimator 2316 having multiple apertures similar to that shown in FIG. 16 and a detector 2322.

The cameras 2320 are mounted on pivots, or hinges 2312, on legs 2311, so that cameras 2320 can be tilted so as to scan at various angles with respect to axis of the breast 2304. A sliding mechanism 2309 on shaft 2302 allows cameras 2320 to be adjusted closer together or further apart. A slot 2313 on each of legs 2311 allows cameras 2320 to be moved up and down along axis A.

FIG. 23 illustrates the collimator field of view when cameras 2320 are at 30 degrees with respect to axis A. Data acquired using this configuration includes gamma events occurring within the breast, near the chest wall. Optionally, length L of cameras 2320 is sufficiently long so that at a 30 degrees tilt, its projection covers the complete diameter of interest, D, at the base of breast 2304. However, small or larger tilt angles may be used if required to cover the breast near the wall. Preferably, as small an angle as possible is used. In this manner, chest wall information is acquired with no loss in spatial resolution. However, a second rotational pass should be made for SPECT analysis of the breast itself. Alternatively, the gamma ray activity is calculated using only the angulated camera configuration.

In some embodiments, length L of camera 2320 is shorter than breast height H. When this happens, several rotational passes are made with cameras 2320 parallel to breast axis A, at different breast "heights", as mounting hinges 2312 of cameras 2320 are moved down slots 2313 of legs 2311. A radiolucent, protective cup or cap 2316 is put on the breast 2304, to protect it from contact with the moving detectors. In exemplary embodiments of the invention, the length L of the camera is between 10 and 15 cm square and it is about 10-15 cm apart. Preferably, a size about 12 cm square is suitable.

Although the embodiments that have been described with reference to a dual-camera SPECT systems, other camera-based SPECT systems are possible. For example, the SPECT systems may comprise single scintillation camera. Alternatively, three or four scintillation cameras, arranged around the axis of rotation, may be used in order to enhance the system sensitivity.

In some embodiments of the invention, the camera-based SPECT system comprises at least one NaI(T1) crystal and an array of PMTs for position sensitivity. Alternatively, the camera-based SPECT system comprises at least one pixelated solid-state scintillation crystal, which is smaller and more suitable to the small and cramped circumstances. Alternatively, it may comprise a single position sensitive PMT. As a further alternative, a semiconductor detector is preferably used.

The collimator 2316 as noted above is similar to that shown in FIG. 16 and sized to cover the detector 2322. Making reference to the reference numerals in FIG. 16, the number of apertures 1303 and associated first septa 1304 are coordinated with the size of the second septa 1506 and associated septa walls 1509. The first septa 1304 is telescopically adjusted relative to the second septa 1506 by any suitable means. One example of such means is similar to that shown in FIG. 8 using at least one electric motor with a threaded shaft, preferably one on each corner of the top plate 1303, where the motors are synchronized in movement.

Features of the adjustable collimators of the present invention include:
1. Adjusting the focal length of the collimator by various means, for example, (a) extending or contracting the first septa relative to a stationary second septa, (b) axially moving the detector within a septa, (c) using aperture tubes of varying lengths that are attached to the top plate of the collimator, and (d) combinations of these.
2. Sensitivity and resolution is controlled by the focal length "f". There is no need for collimator exchange depending on imaging options. Alternatively, due to the resolution and sensitivity characteristics of an adjustable system according to the present invention, the changing out of collimators is at least minimized or reduced compared to fixed collimators.
3. Projection area is matched with detector surface area by adjusting the focal length. Thus, dead space on detector can be reduced to zero. Typical pinhole without septa provides conical-shaped projections that result in dead space at the detector corners.
4. Easy control of FOV by controlling acceptance angle.
5. Can be used with multi-pinhole collimator with septa application.

It is believed that the adjustable focal length will lead to significant cost benefit compared to conventional collimation where multiple sets of collimators are needed for different imaging and isotope energies. The invention especially provides great freedom compared to ring-type system design.

What is claimed is:

1. A collimator for use with a detector of nuclear radiation, where the detector has a top surface, comprising:

a collimator surface having at least one aperture located in a plane parallel to the top surface, wherein when the collimator is used with the detector, the plane and the top surface are spaced apart by a focal distance f; and at least one collimator septum defining the side wall or walls of the collimator; and means for changing the focal distance f to adjust the focal length of the collimator, wherein the at least one collimator septum is a first septal tube and wherein the means for changing the distance f comprises the first septal tube, a top plate with a centrally located threaded hole, and an aperture tube having male threads, a first opening and a second opening, wherein the aperture tube threadedly engages the threaded hole, and the top plate is secured to one end of the first septum opposite the top surface, and wherein the at least one aperture is the first opening, which is opposite the top surface and changing the relative position of the first opening to the top surface changes the focal distance f.

2. The collimator of claim 1, wherein the at least one collimator septum comprises a first septal tube and a second septal tube smaller in cross-section than the first septal tube such that the second septal tube is received within the first septal tube, and wherein the means for changing the distance f is means for changing the relative position of the second septum within the first septum.

3. The collimator of claim 2, wherein the means for changing the relative position of the second septa within the first septa is a cam and cam follower assembly.

4. The collimator of claim 2, wherein the means for changing the relative position of the second septum within the first septum is female threads on the first septum and male threads on the second septum, wherein the female and male threads are threadedly engaged.

5. The collimator of claim 2, wherein the means for changing the relative position of the second septum within the first septum comprises a positioner having an actuator and a rod, wherein the actuator is secured to one of said first and second septa, and the rod is secured to the other of the first and second septa.

6. The collimator of claim 5, wherein the positioner further comprises a tab having a threaded hole, and
wherein the actuator is an electric motor that rotates the rod and the rod has threads on one end that threadedly engages the threaded hole, thereby securing the rod to the other of the first and second septa and as the motor rotates, the relative position of the first and second septa is changed.

7. The collimator of claim 2, wherein the cross-section of the first and second septa is selected from the group of circle, square, rectangle and other polygons.

8. The collimator of claim 1,
wherein the at least one aperture is a plurality of apertures, wherein the at least one collimator septum comprises
a plurality of first septal tubes and
a corresponding plurality of second septal tubes smaller in cross-section than the first septal tube such that the second septal tube is received within the first septal tube,
wherein the collimator has top plate with the plurality of apertures and a corresponding one of the plurality of first septa attached to the top plate centered around each of the plurality of apertures,
wherein the means for changing the distance f comprises means for changing the relative position of each of the plurality of second septa within a corresponding one of the plurality first septa.

9. The collimator of claim 1, wherein the collimator has a top plate with the at least one aperture and is located opposite said top surface.

10. The collimator of claim 9, wherein the at least one aperture is a single aperture.

11. The collimator of claim 9, wherein the top plate is removable and replaceable with a second top plate having a different sized aperture than the removed top plate.

12. A detection system for nuclear radiation, comprising:
a nuclear radiation detector having at least one edge and a top surface;
a collimator having a collimator surface having an aperture located in a plane parallel to the top surface, wherein the plane and the top surface are spaced apart by a focal distance f; and
at least one collimator septa defining the side wall or walls of the collimator; and means for changing the focal distance f to adjust the focal length of the collimator,
wherein the at least one septa is a first septa tube and
wherein the means for changing the distance f comprises the first septa tube, a top plate with a centrally located threaded hole, and an aperture tube having male threads, a first opening and a second opening,
wherein the aperture tube threadedly engages the threaded hole, and the top plate is secured to one end of the first septa opposite the top surface, such that the first opening is opposite the top surface and changing the relative position of the first opening to the top surface changes the focal distance f.

13. The collimator of claim 12, wherein the means for changing the distance f comprises means for moving the detector normal to the plane.

14. The collimator of claim 12, wherein the collimator comprises the means for changing the distance f.

15. The collimator of claim 14, wherein the means for changing the distance f comprises a first septal tube, a second septal tube smaller in cross-section than the first septal tube such that the second septal tube is received within the first septal tube, and
means for changing the relative position of the second septal tube within the first septal tube.

16. The collimator of claim 15, wherein the means for changing the relative position of the second septal tube within the first septal tube is a cam and cam follower assembly.

17. The collimator of claim 15, wherein the means for changing the relative position of the second septal tube within the first septal tube is female threads on the first septal tube and male threads on the second septal tube, wherein the female and male threads are threadedly engaged.

18. The collimator of claim 15, wherein the means for changing the relative position of the second septal tube within the first septal tube comprises a positioner having an actuator and a rod, wherein the actuator is secured to one of said first and second septa, and the rod is secured to the other of the first and second septa.

19. The collimator of claim 18, wherein the positioner further comprises a tab having a threaded hole, and
wherein the actuator is an electric motor that rotates the rod and the rod has threads on one end that threadedly engages the threaded hole, thereby securing the rod to the other of the first and second septa and as the motor rotates, the relative position of the first and second septa is changed.

20. The collimator of claim 15, wherein the cross-sections of the first and second septa are selected from the group of circle, square, rectangle and other polygons.

21. The collimator of claim 12, wherein the collimator has a top plate with an aperture and is located opposite said top surface.

22. The collimator of claim 21, wherein the top plate is removable and replaceable with a second top plate having a different sized aperture than the removed top plate.

23. The collimator of claim 12, wherein the nuclear radiation detector is a semiconductor detector.

24. The collimator of claim 12, wherein the nuclear detector is a scintillation crystal.

25. A nuclear imaging system, comprising at least one detection system comprising:
A detection system for nuclear radiation, comprising:
a nuclear radiation detector having at least one edge and a top surface;
a collimator having a collimator surface having an aperture located in a plane parallel to the top surface, wherein the plane and the top surface are spaced apart by a focal distance f; and
at least one collimator septa defining the side wall or walls of the collimator; and means for changing the focal distance f to adjust the focal length of the collimator,
wherein the at least one septa is a first septa tube and
wherein the means for changing the distance f comprises the first septa tube, a top plate with a centrally located threaded hole, and an aperture tube having male threads, a first opening and a second opening,
wherein the aperture tube threadedly engages the threaded hole, and the top plate is secured to one end of the first septa opposite the top surface, such that the first opening is opposite the top surface and changing the relative position of the first opening to the top surface changes the focal distance f,
wherein the nuclear imaging system comprises a hand-held device.

26. The nuclear imaging system of claim 25, wherein the nuclear imaging system is portable.

27. The nuclear imaging system of claim 25, wherein the nuclear imaging system is for the nuclear imaging of a woman's breast and the at least one detection system is of a size appropriate for the scanning of the breast.

28. The nuclear imaging system of claim 25, wherein the nuclear imaging system includes means for selectively tilting the at least one detection system such that the top surface is selectively tilted or parallel to the axis of the breast.

29. The nuclear imaging system of claim 25, wherein the nuclear imaging system has at least two detection systems.

* * * * *